United States Patent
Choe et al.

(10) Patent No.: US 6,440,276 B2
(45) Date of Patent: Aug. 27, 2002

(54) PROCESS FOR PRODUCING THIN FILM GAS SENSORS WITH DUAL ION BEAM SPUTTERING

(75) Inventors: Yong Sahm Choe; Jae Ho Chung, both of Seoul; Dae Seung Kim, Suwon-shi, all of (KR)

(73) Assignee: Tong Yang Moolsan Co., Ltd., KRX ( * ) Notice: Subject to any disclaimer, the term of this patent is extended or adjusted under 35 U.S.C. 154(b) by 0 days.

(21) Appl. No.: 09/761,286

(22) Filed: Jan. 16, 2001

Related U.S. Application Data (63) Continuation of application No. 09/266,983, filed on Mar. 12, 1999, now abandoned.

(30) Foreign Application Priority Data

Feb. 9, 1999 (KR) .............................. 99-4453

(51) Int. Cl.$^7$ .............................. C23C 14/34
(52) U.S. Cl. .............. 204/192.11; 204/192.25
(58) Field of Search ........... 204/192.25, 192.11, 204/192.15

(56) References Cited

U.S. PATENT DOCUMENTS

| | | |
|---|---|---|
| 5,540,808 A | 7/1996 | Vincent et al. |
| 5,618,496 A | 4/1997 | Hasumi et al. |

FOREIGN PATENT DOCUMENTS

| | | | |
|---|---|---|---|
| JP | 9-170993 | 6/1930 | |
| JP | 02 088 762 A | * 3/1990 | ............ 204/192.11 |

OTHER PUBLICATIONS

Suzuki et al. "Influence of thickness on $H_2$ gas sensor properties in polycrystalline $SnO_x$ films prepared by ion–beam sputtering", Journal of Materials Science 23 (1988) pp. 1106–1111.

Tamaki et al., "Dilute hydrogen sulfide sensing properties of $CuO–SnO_2$ thin film prepared by low–pressure evaporation method" Sensors and Actuators, B 49 (1998) pp. 121–125.

Maekawa et al. "Sensing Behavior of $CuO$–Loaded $SnO_2$ Element of $H_2S$ Detection", Chemistry Letters, p. 575 (1991).

Chung et al., "Tin oxide microsensor for LPG monitoring" Sensors and Actuators B, 20 (1994) pp. 139–143.

Rumyantseva et al. "Copper and nickel doping effect on interaction of $SnO_2$ films with $H_2S$", J. Master Chem., 1997, 7(9) pp. 1785–1790.

Suzuki et al., "Thickness dependence of $H_2$ gas sensor in amorphous $SnO_x$ films prepared by ion–beam sputtering", Journal of Materials Science 23, (1988) pp. 145–149.

Tamaki et al., "$CuO–SnO_2$ element for highly sensitive and selective detection of $H_2S$", Sensors and Actuators, B9 (1992), p. 197.

Noboru Yamazoe Sensor & Actuator B, 5 (1991) pp. 7–19.

* cited by examiner

*Primary Examiner*—Nam Nguyen
*Assistant Examiner*—Gregg Cantelmo
(74) *Attorney, Agent, or Firm*—Akerman Senterfitt (57) ABSTRACT

A process for making a stoichiometric and crystalline thin film CuO catalytic layer atop a gas sensing layer for the detection of dilute sulfur compound gases. The sensing layer is made using dual ion beam sputtering, where an argon ion beam sputters targets comprising Sn or its oxides, and a pure or highly concentrated oxygen ion beam is simultaneously deposited on a substrate. The catalytic layer is made using dual ion beam sputtering, where an argon ion beam sputters targets comprising CU or its oxides, and a pure or highly concentrated oxygen ion beam is simultaneously deposited on a substrate.

4 Claims, 10 Drawing Sheets

PROCESS FOR PRODUCING THIN FILM GAS SENSORS WITH DUAL ION BEAM SPUTTERING

CROSS REFERENCE TO RELATED APPLICATIONS

This application is a continuation of U.S. patent application Ser. No. 09/266,983, now abandoned, which was filed with the United States Patent and Trademark Office on Mar. 12, 1999.

BACKGROUND OF THE INVENTION

1. Field of the Invention

The present invention generally relates to a method of preparing thin film gas sensors. It more particularly relates to a gas-sensing layer of $SnO_2$ thin-film for stable detection of reducing gases. It also relates particularly to thin film CuO catalytic layer for the detection of dilute sulfur compound gases.

2. Description of Prior Art

Various forms of $SnO_2$, including sintered block, thick film, and thin film, have widely been researched and used as gas sensors for hydrogen, hydrocarbons, carbon monoxide, and nitrous oxides. Recently, thin film gas sensors attracted a lot of industrial and scientific attention due to their high sensitivity and possibility of integration. In producing $SnO_2$ thin films, it is important to avoid formation of amorphous and intermediate phases such as Sn or SnO, which may adversely affect the sensor characteristics.

Takeyuki Suzuki et al. deposited $SnO_{2-x}$ thin films by sputtering $SnO_2$ target with argon ion beam (Journal of Materials Science 23, 1988, 145–149, Journal of Materials Science 23, 1988, 1106–1111). In this report, the substrate temperature was below 100° C., and the resulting films were amorphous and nonstoichiometric. Therefore, an intermediate phase of $Sn_3O_4$ was formed after a heat treatment at 300° C., and the hydrogen sensitivity of the sensor was very low. Wan-Young Chung et al. deposited $SnO_2$ thin films on Si wafers through thermal evaporation and subsequent thermal oxidation of Sn films (Sensors and Actuators B, 20, 1994, 139–143). The research reported detachment of the film from wafers after thermal oxidation, which was caused by large volume expansion during oxidation and phase transformation. Seok-Keun Koh et al. used reactive ionized cluster deposition to produce $SnO_2$ films at room temperature (Japan Patent 9-170993). The oxygen ion beam used in the patent produced amorphous and nonstoichiometric films at accelerating voltage as high as 4 kV.

In the case of CuO with p-type conductivity, it has been known that its addition to $SnO_2$ greatly increases the sensitivity and selectivity to hydrogen sulfide (T. Maekawa et al., Chem Lett., 1991 (1991) 575, J. Tamaki et al., Sensors and Actuators, B9 (1992) 197, M. Rumyantseva et al., J. Mater. Chem., 1997, 7(9) 1785–1790). This type of sensor is reported to have stable and excellent sensing characteristics to hydrogen sulfide in the concentration range between 10 to 100 ppm at 200° C.

The excellent sensing characteristics of CuO-added $SnO_2$ to hydrogen sulfide is ascribed to p-n function formed between n-type $SnO_2$ and p-type CuO. The p-n junction builds very high electrical resistance across the interface by forming a thick charge depletion layer on each side. When CuO is exposed to sulfur compound gases such as hydrogen sulfide, it is converted to CuS with metallic conductivity through chemical reactions as in the example shown below:

$$CuO + H_2S \rightarrow CuS + H_2O$$

$$CuO + CH_3SH + 3/2\ O_2 \rightarrow CuS + CuO + 2H_2O$$

Consequently, the p-n junction as well as the charge depletion layer shall disappear causing the resistance of the sensor to drop dramatically.

The sensors described above performed excellent sensing characteristics to hydrogen sulfide at a concentration higher than 10 ppm, but was very poor at a lower concentration. To solve this problem, various attempts have been made, such as fine distribution of CuO through chemical fixation method or thin film deposition with spin coating or vacuum evaporation. These attempts succeeded in lowering the detection range to a few ppm or to 0.1~0.3 ppm, but the sensitivity is still less than around 10. Kazuhisa Hasumi et al. produced $CuO$—$SnO_2$ type hydrogen sulfide sensor through thick film technology and spin coating (U.S. Pat. No. 5,618,496). J. Tamaki et al. produced gas sensors with sensitivity of 8.8 to hydrogen sulfide of 0.2 ppm through evaporation and thermal oxidation of Sn and Cu (Sensors and Actuators, B 49 (1998) 121–125). This sensor is reported to show sensitivity to hydrogen sulfide of 0.02 ppm, but the value was quite low, and the response time was as long as 10 minutes.

SUMMARY OF THE INVENTION

It is, therefore, an object of the present invention to provide stoichiometric, dense, highly electrically resistant and crystalline $SnO_2$ thin films at low substrate temperature showing excellent sensing characteristics to reducing gases. It is also an object of the present invention to provide stoichiometric, dense and crystalline CuO thin films capable of detecting dilute sulfur compound gases.

It is a further object to provide the process by which stoichiometric, dense, highly resistant and crystalline thin film $SnO_2$ gas sensing layer of the present invention to be made. It is also a further object to provide the process by which stoichiometric, dense and crystalline thin film CuO catalytic layer of the present invention to be made.

BRIEF DESCRIPTION OF THE DRAWINGS

The invention will be described further in conjunction with the accompanying drawings, in which.

DETAILED DESCRIPTION OF THE INVENTION

The present invention discloses stoichiometric, dense, highly resistant and crystalline $SnO_2$ thin films and the process for making them. The films themselves are useful for highly sensitive gas sensing layers capable of stably detecting reducing gases. It also discloses stoichiometric, dense, and crystalline CuO thin films and the process for making them. The films themselves are useful for highly sensitive catalytic layers capable of detecting dilute sulfur compound gases.

The processes by which the present films are made is new in that an argon ion beam sputters targets and another pure or highly concentrated oxygen ion beam is simultaneously deposited with energy lower than 500 eV on the substrate. The films produced by the present method have stoichiometric compositions and dense crystalline microstructures.

The present process comprises: sputter-depositing atoms from a Sn or Cu or their oxide targets onto a substrate using argon sputter ion gun and, simultaneously depositing oxygen atoms using an oxygen assist ion gun onto the substrate until thin film of desired thickness is obtained.

Figure 1:
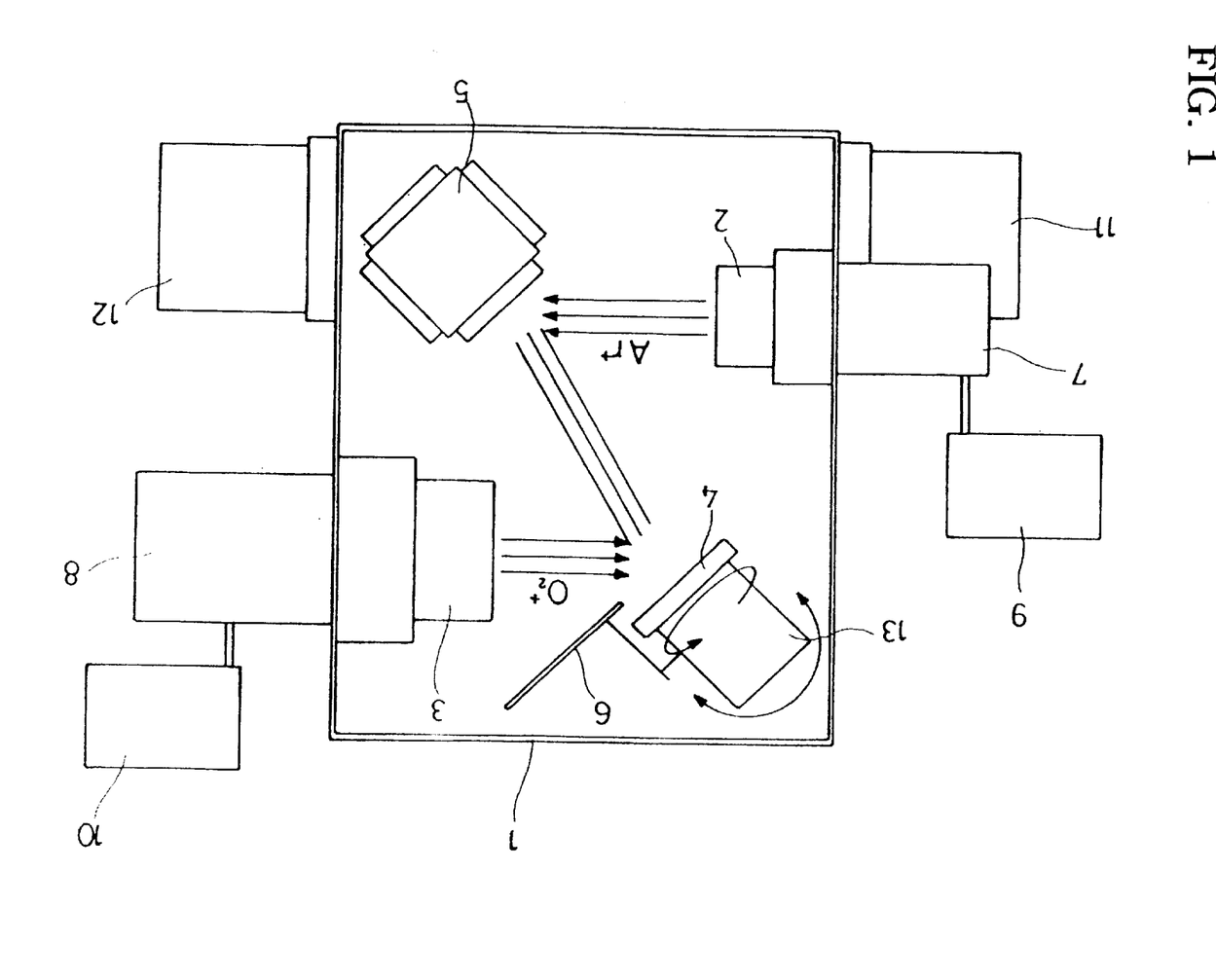
FIG. 1 is a drawing of components of the fabrication process.

FIG. 1 is a drawing of the fabrication process components. The dual ion beam sputtering basically consists of 2 ion guns (sputter gun 2 and an assist gun 3), a target 5, and a substrate 4.

When in use, the vacuum chamber is evacuated by a vacuum pump or two 11 and 12 to maintain high vacuum. Inside the vacuum chamber, the sputter ion gun 2 is positioned facing the target 5, which is tilted at a 45° angle from the ion beam direction and aligned parallel to the substrate 4. An RF generator 7 is located outside the vacuum chamber. The substrate 4 is again tilted at 45° angle from the ion beam direction of the assist gun 3. The assist gun 3 is a filamentless type which can efficiently and stably generate oxygen plasma. In the present invention, an external RF generator 8 is used in place of a filament.

As a dual ion beam sputtering consists of two separate ion guns, one of which is the main gun (or sputter gun) to sputter targets, and the other of which is assist gun to supply oxygen ion beam, it is possible to precisely and independently control sputter rate and oxygen assist energy.

While both the gridded and gridless ion guns meet the purpose of the present invention, the gridded type is preferred as the main gun to sputter targets. The gridded ion gun is able to generate highly dense and efficient ion beams, and the deposited films show a fast nucleation and relatively dense structure due to energetic impingement of sputtered atoms by a few eV.

In producing dense and stoichiometric $SnO_2$ thin films and CuO thin films, the sputter ion beam must have desirable values of acceleration energy and an ion beam current density. In the present invention, a process wherein the acceleration energy and the current density of the sputter ion beam are from 0.5 keV to 2.0 keV and from 0.5 mA/cm$^2$ to 5 mA/cm$^2$, respectively, is preferred. With either of the acceleration energy or the current density lower than the said minima, flux of the sputtered atoms is so small that resputtering effect of the assist beam makes the deposition either virtually ineffective or inconveniently slow. On the other hand, with either of the two process values higher than the said maxima, the excessive sputtering energy causes nonstoichiometric composition or damage to the targets.

Targets used in the present invention may be either metal or metal oxides, and each has its own relative advantages. The most important advantage of oxide targets is the availability of highly resistive and crystalline thin films with lower assist energy, which is the result of Sn—O or Cu—O bond already existing in sputtered species. On the other hand, while metal targets tend to produce films with lower resistivity and crystallinity at the same energy value as with oxide targets, they give higher productivity through increasing deposition rate by 4 or 5 times. Besides, the difference of properties between films made from metal targets and oxide targets is not so high that it may possibly be compensated through treatments such as annealing.

The effect of the assist ion gun in the present invention is described below. It is well known that, for the deposition of oxide thin films, substrate temperature is required to be as high as a few hundred degrees celsius. As the energy of the assist ion beam has a similar effect to that of heat energy, the use of assist ion beam makes it possible to deposit oxide thin films without heating substrates. Plasma in an ion beam is a group of highly energetic gas species that are highly reactive. When irradiated on to the substrate, these highly excited and reactive ions increase the atomic mobility in films during deposition and thus help improve crystallinity and the density of the films. In the present invention, the effect of the oxygen assist ion beam made it possible to deposit $SnO_2$ and CuO thin films with relatively low assist energy of 500 eV at the substrate temperature below 100° C. The value of assist acceleration voltage is an important factor in determining thin film's crystallinity, orientation, stoichiometry, etc.

The processes by which the present films are made is new also in that the assist ion beam gun uses pure oxygen or oxygen-argon mixture with oxygen concentration higher than 50%. In the mixture, oxygen contributes to the oxide formation while argon to plasma maintenance and film densification with higher kinetic energy. The argon, however, may remain in the deposited films as a source of remnant stress or cause oxygen deficiency by selective resputtering of oxygen atoms. Therefore, pure oxygen ion beam is the most preferred in the present invention, and the argon content, in any case, should not be higher than 50%.

The most important contribution of the described assist ion beam effect to the function of gas sensors is as follows; the assist ion beam produce films of denser structure which leads to thicker charge depletion layer. As a result, the film has higher resistivity and, therefore, a higher sensitivity.

Semiconductor-type gas sensors, such as $SnO_2$, detect target gases through electrical resistance change before and after gas molecules react with and detach adsorbed oxygen from the sensor surface. In the case of porous polycrystalline, it is reported that the sensor shows high sensitivity when diameter of a grain is smaller than twice the Debye length which represents thickness of depletion layer (Noboru Yamazoe, New approaches for improving semiconductor gas sensors, Sensor & Actuator B, 5 (1991) 7–19). As the typical Debye length was known to be 3 nm for a porous body, it was needed to reduce grain size to less than 6 nm.

Figure 2:
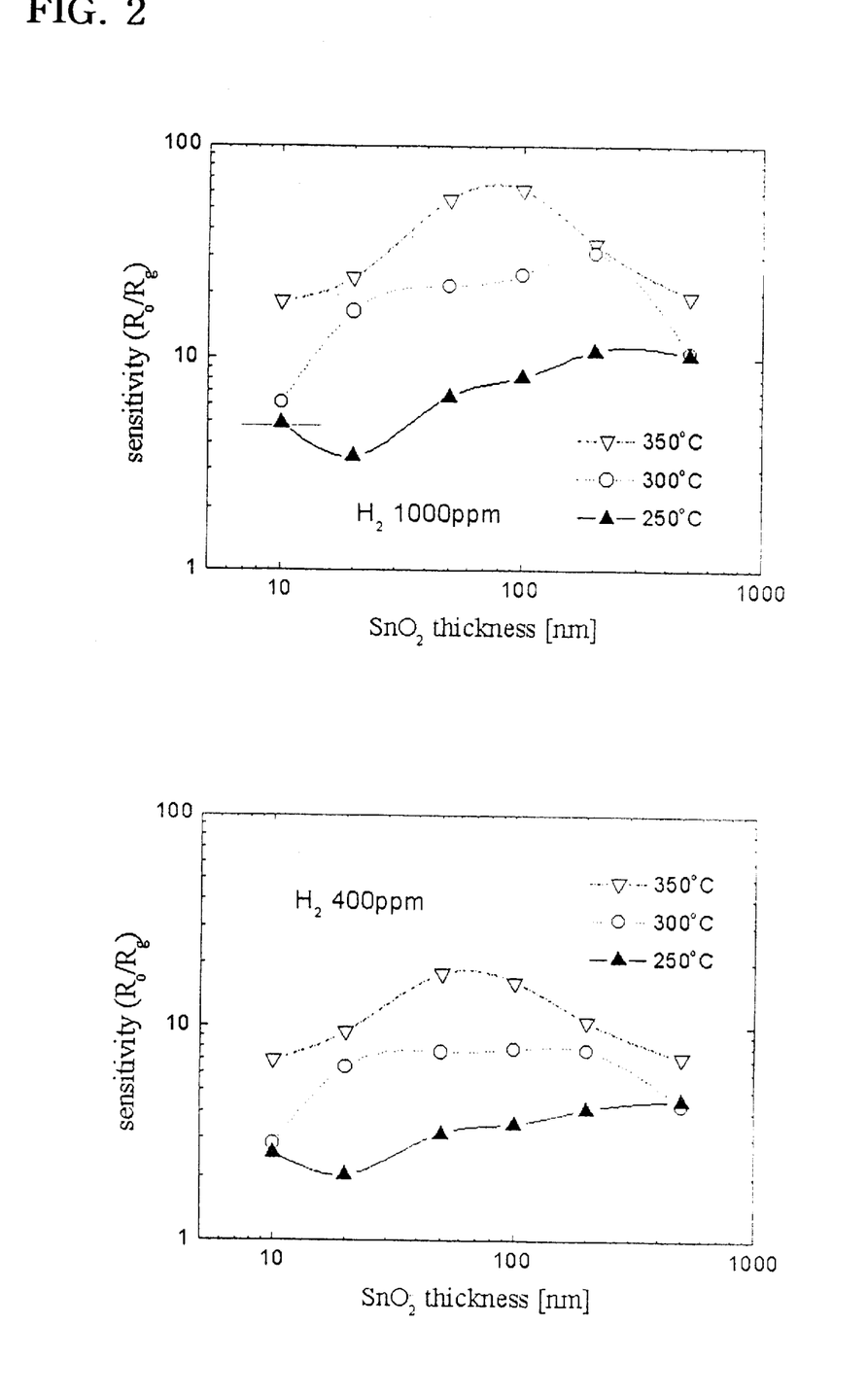
FIG. 2 is a plot of the hydrogen sensitivity of $SnO_2$ films as a function of film thickness at various temperatures. The sensitivity is a ratio of the sensor's gas-induced resistance ($R_g$) to initial resistance ($R_o$)

In the present invention, the effect of assist ion beam on densification and crystallization made it possible to produce highly resistance $SnO_2$ thin films, not by reducing grain size, but by increasing the Debye length up to the thickness of a film. To estimate depletion layer thickness in $SnO_2$ thin films of the present invention, hydrogen sensitivity of the films of several thickness between 10 nm and 500 nm were measured at different temperatures as shown in FIG. 2. In the figure, it is shown that optimum thickness for highest sensitivity, which is closely related with depletion layer thickness, exists and changes depending on the temperature. The optimum thickness was formed around 100 nm, and it shows that the films deposited by the present process have very thick depletion regions. As a result, while films as thin as a few nm may have durability or stability problems, the films in the present invention with thickness of around 100 nm have both high sensitivity and stability.

For example, and not by way of limitation, the following may be helpful in elucidating the present invention. In giving examples of detailed dual ion beam sputtering process of $SnO_2$ and CuO thin films, it is described basically with respect to producing $SnO_2$ thin films as CuO films can also be produced in similar ways.

EXAMPLE 1

Deposition of Stoichiometric, Highly Resistance and Crystalline $SnO_2$ Thin Films An insulating substrate 4 was cleaned by detergent and deionized water, dried and attached to substrate holder 13. The target 5 composed of Sn or its oxides was water-cooled to avoid overheating during ion beam sputtering. After the chamber was evacuated to less than $2.0 \times 10^{-6}$ Torr, argon was supplied to and RF plasma generated in the assist gun 3 to clean the substrate with ion beam acceleration energy and current density of 300 eV and 0.5 mA/cm$^2$, respectively. The angle between the surface of the substrate 4 and the ion beam incident direction was about 70°, and the substrate holder 13 was rotated to help uniform cleaning. The shutter 6 was closed when the ion cleaning finished. Argon was supplied to the sputter gun 2 from an argon source 9, and an ion beam with acceleration energy and current density of 0.5~2.0 keV and 0.5~5.0 mA/cm$^2$, respectively, was generated to sputter the target 5. Simultaneously, oxygen was supplied to the assist gun 3 from an oxygen source 10, and an ion beam with acceleration energy of 0~500 eV generated and directed to the substrate 4. After each ion gun was stabilized, the shutter 6 was opened and thin films were deposited on the substrate up to a desired thickness. During the process, the substrate 4 was rotated to ensure uniform deposition.

The deposition process was followed by annealing at a temperature higher than 350° C. for over 2 hours for the purpose of enhancing crystallinity and stability. The annealing condition can be selected with respect to sensor's desired initial resistance and sensing characteristics. A temperature between 350° C. and 600° C. was preferred for annealing, as lower temperature was not enough for stabilization and higher temperature might reduce resistivity and sensitivity. Annealing time between 5 and 10 hours was preferred at the said temperature range. The deposited and annealed $SnO_2$ films were added with catalyst such as Pt or Pd to provide sensitivity and selectivity to target gases.

EXAMPLE 2

Compositional Analysis

Figure 3:
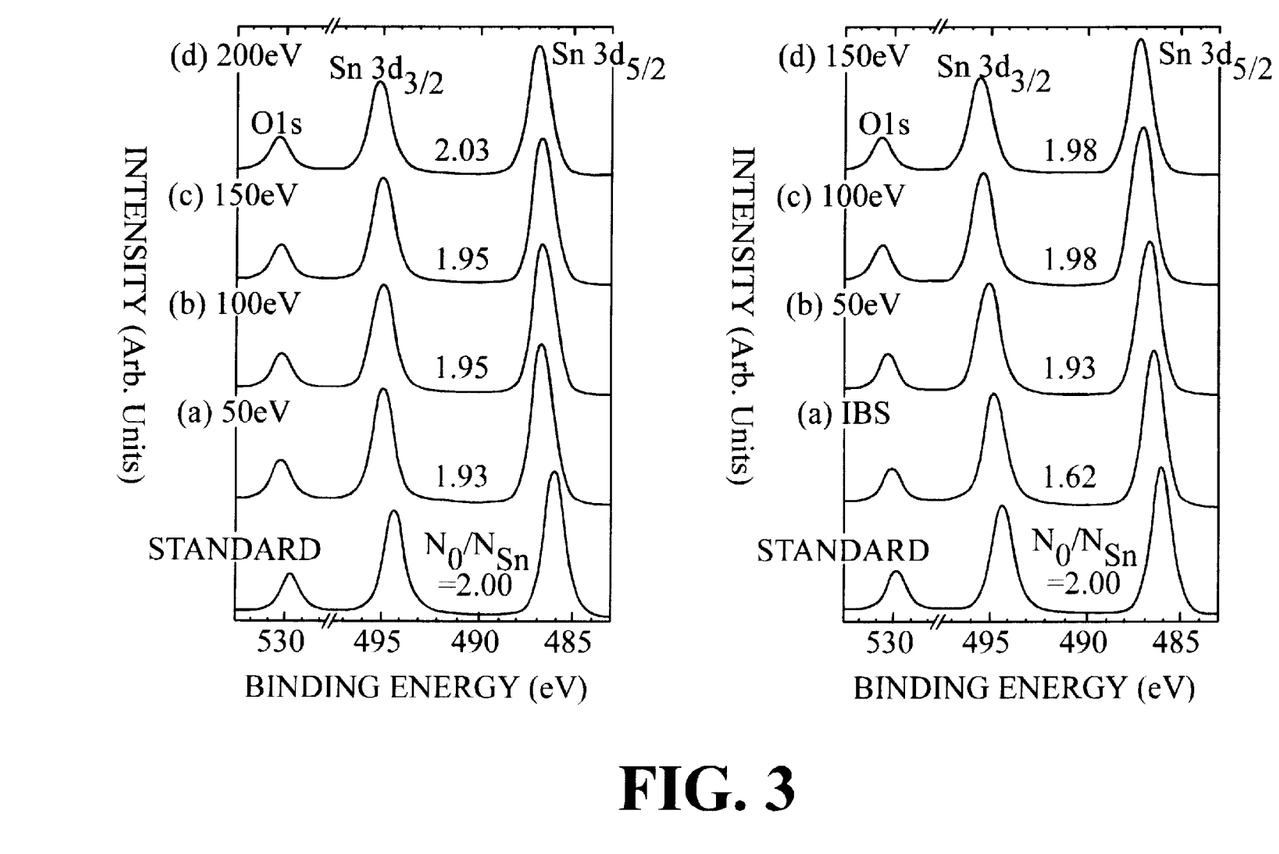
FIG. 3 is a spectra of the XPS (X-ray Photoelectron Spectroscopy) showing chemical bonding energy of $SnO_2$ thin films produced by the process in the present invention.

The stoichiometric composition of the $SnO_2$ films produced on silicon wafers were evaluated by X-ray photoelectron spectroscopy (XPS) and Rutherford backscattering spectroscopy (RBS). FIG. 3 is the XPS spectra of $SnO_2$ thin films deposited from either Sn target or $SnO_2$ target. As can be seen in the figure, all of the films deposited using oxygen assist ion beam had O:Sn ratios higher than 1.9:1, which increased up to a nearly stoichiometric composition of 2.0:1 with an increase of acceleration voltage.

EXAMPLE 3

Crystallinity Analysis

Figure 4:
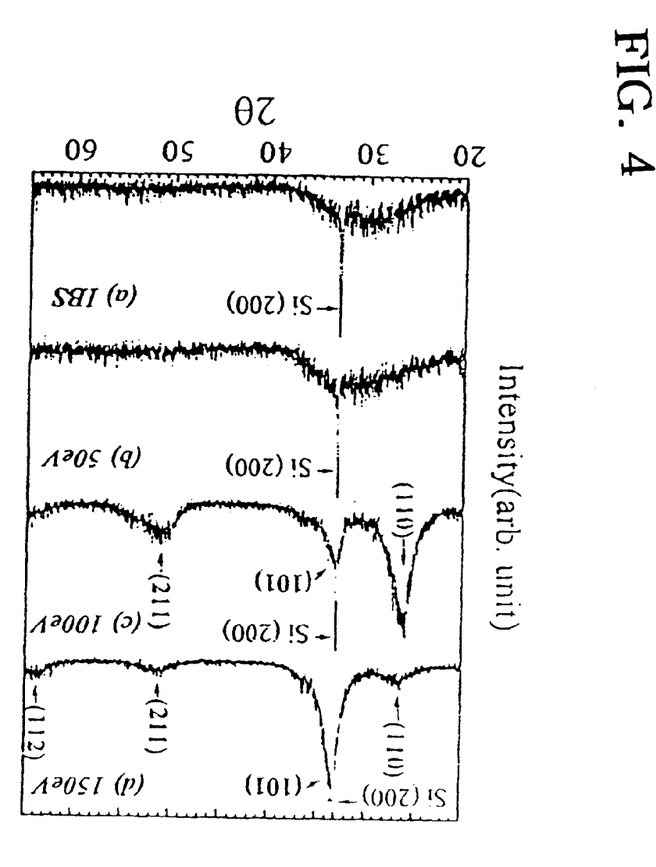
FIG. 4 is a spectra of the XRD (X-Ray Diffraction) showing a crystallinity of $SnO_2$ thin films produced by the process in the present invention.
Figure 5:
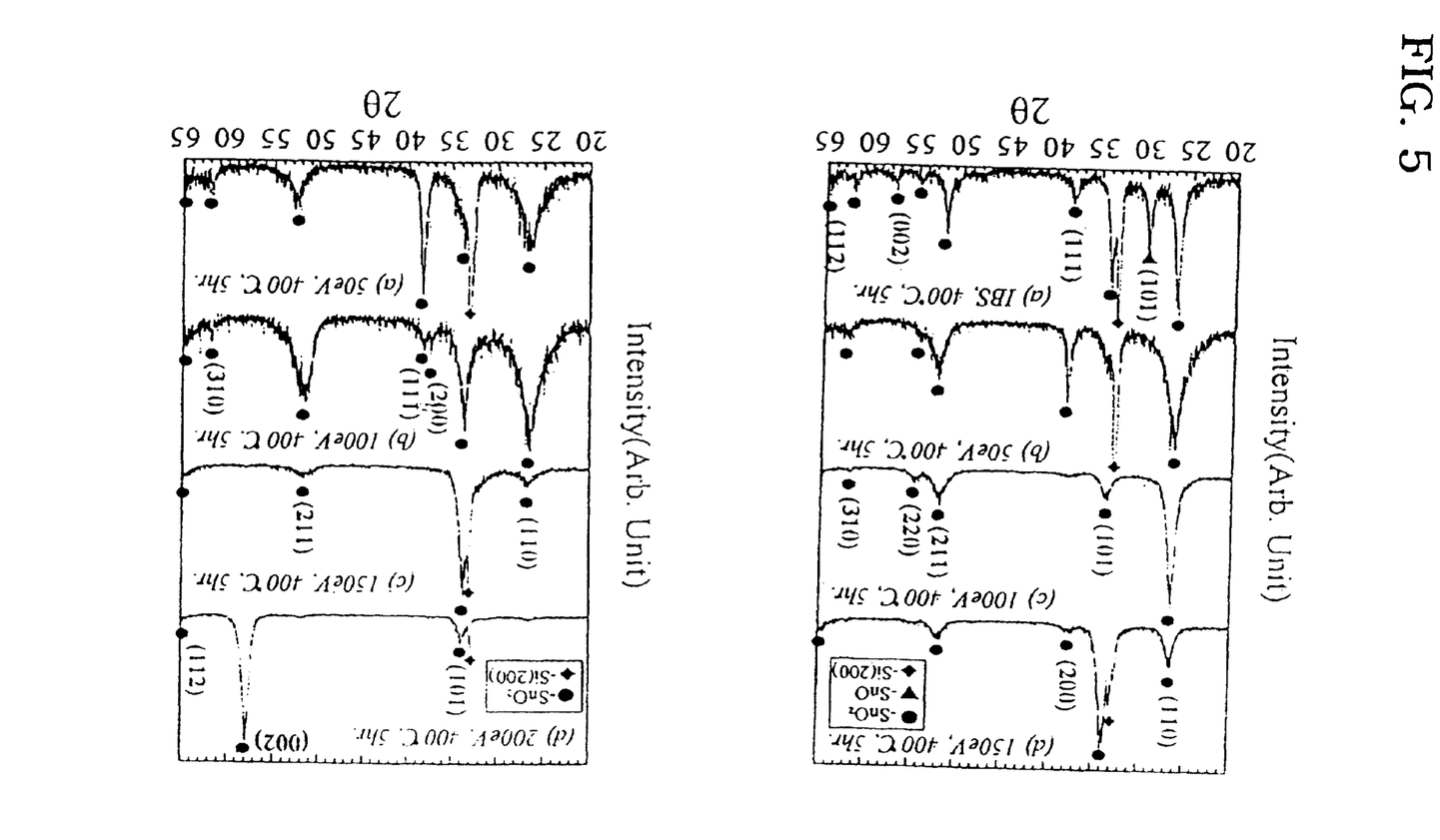
FIG. 5 is a spectra of the XRD (X-Ray Diffraction) showing a crystallinity of $SnO_2$ thin films produced by the process in the present invention and annealed at 400° C.

The crystallinity of the $SnO_2$ films and CuO films produced on silicon wafers were evaluated by X-ray diffraction (XRD). FIG. 4 and FIG. 5 are XRD spectra of $SnO_2$ thin films as-deposited and annealed at 400° C., respectively. The film was amorphous at the lowest acceleration energy of 50 eV, and its crystallinity was enhanced and preferred orientation changed as the voltage increased. After annealing at 400° C., the crystalline peaks developed more, but the preferred orientation was not changed. This suggests that no structural change except crystal growth took place during the annealing at 400° C., and that therefore the thin film is very stable. In addition, films deposited using oxygen assist ion beam showed excellent characteristics with no intermediate phases.

Figure 6:
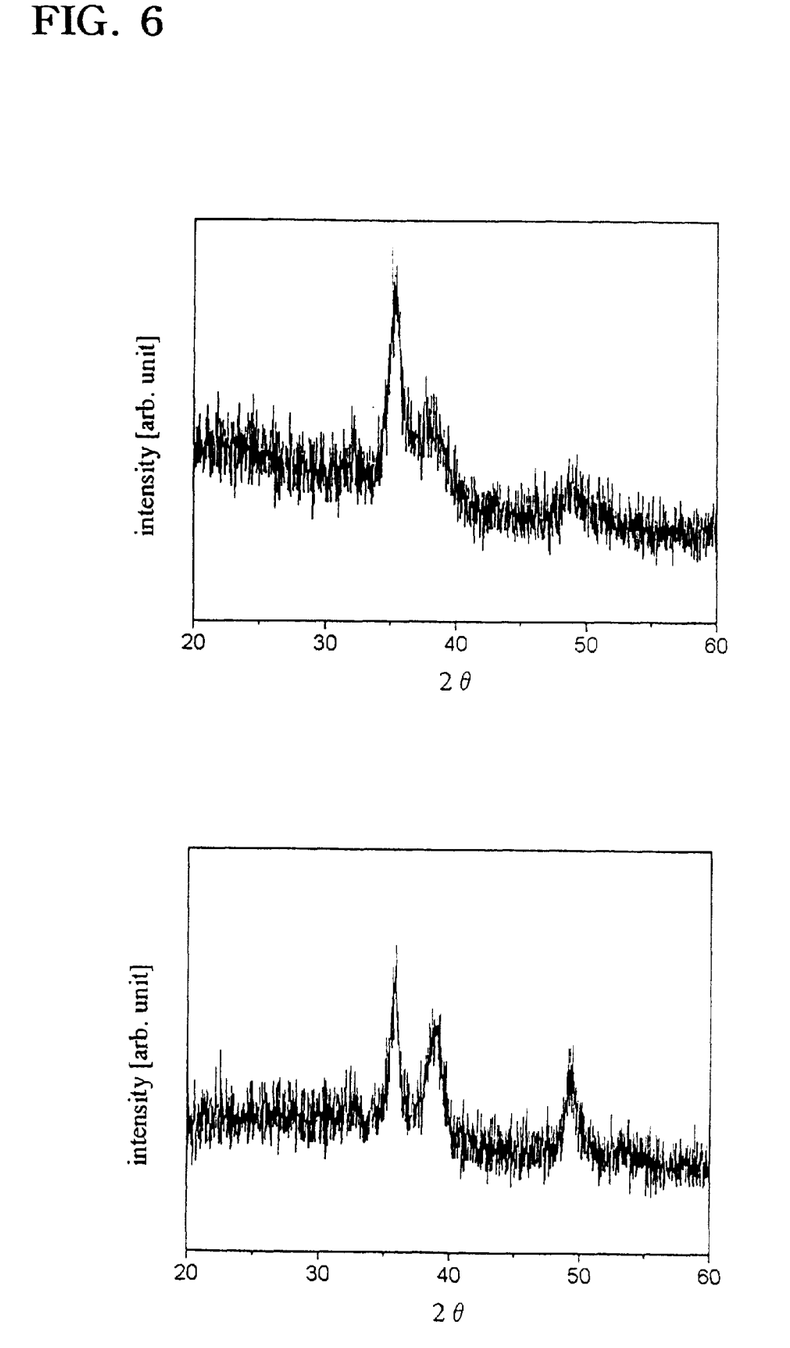
FIG. 6 is a spectra of the XRD (X-Ray Diffraction) showing a crystallinity of CuO thin films produced by the process in the present invention.

FIG. 6 is the XRD spectra of CuO thin films deposited on silicon wafer. It is also very well shown, that the films deposited at room temperature had crystalline phases.

EXAMPLE 4

Microstructure Analysis

Figure 7:
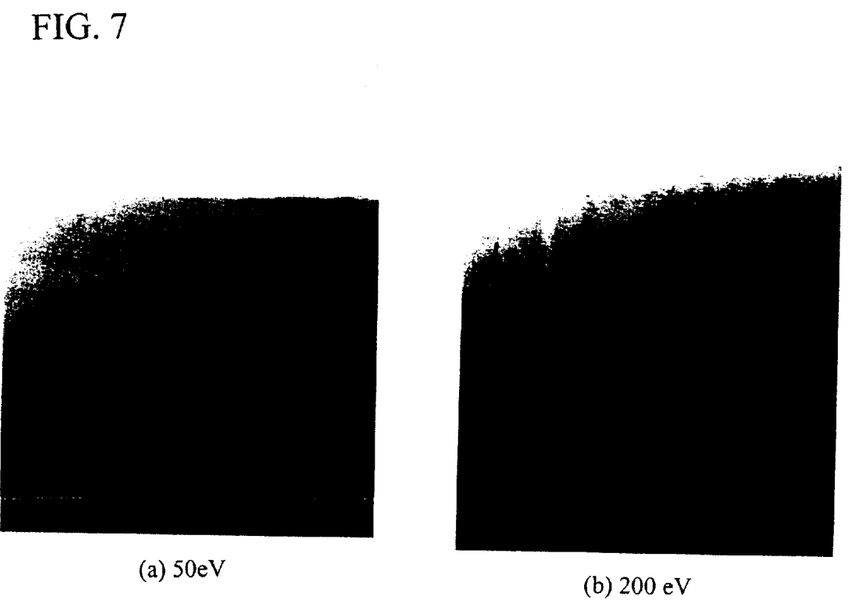
FIG. 7 are micrographs of the XTEM (Cross-sectional Transmission Electron Microscopy) showing the microstructure of $SnO_2$ thin films produced by the process in the present invention.
Figure 8:
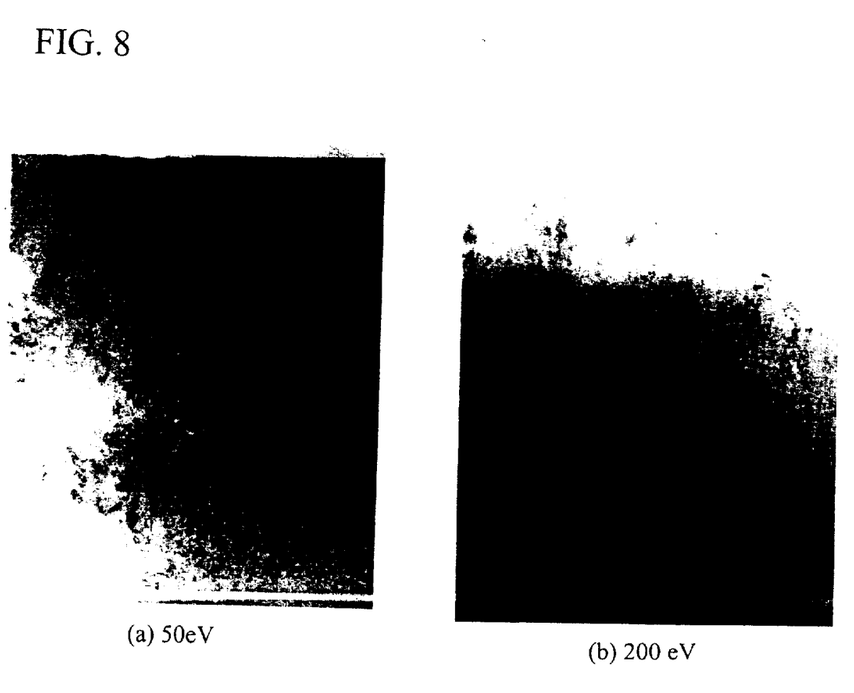
FIG. 8 are micrographs of the XTEM (Cross-sectional Transmission Electron Microscopy) showing the microstructure of $SnO_2$ thin films produced by the process in the present invention and annealed at 400° C.

The microstructure of the $SnO_2$ films produced on silicon wafer was evaluated by cross-sectional transmission electron microscopy (XTEM), and shown in FIG. 7 and FIG. 8. As can be seen in FIG. 7, while the low assist energy of 50 eV produced amorphous structure, the higher energy of 200 eV produced highly dense columnar structure in the film. After annealing, as shown in FIG. 8, while both of the films had well-developed crystalline structure, no conspicuous voids or orientation changes were found. This suggests that the films were deposited as single-phased $SnO_2$ and their stability was maintained during annealing. As the existence of intermediate phases may cause instability of the films during annealing, the single-phased $SnO_2$ thin films produced in the present invention are promising in application as stable gas sensors operating at elevated temperature.

EXAMPLE 5

Surface Morphology Analysis

The surface morphology of the $SnO_2$ films and CuO films produced on silicon wafer was observed with scanning electron microscopy (SEM) and atomic force microscopy (AFM). As the images showed no conspicuous morphology on the surface, its roughness was estimated to be as low as a few angstrom.

EXAMPLE 6

Electrical Resistivity Analysis

Figure 9:
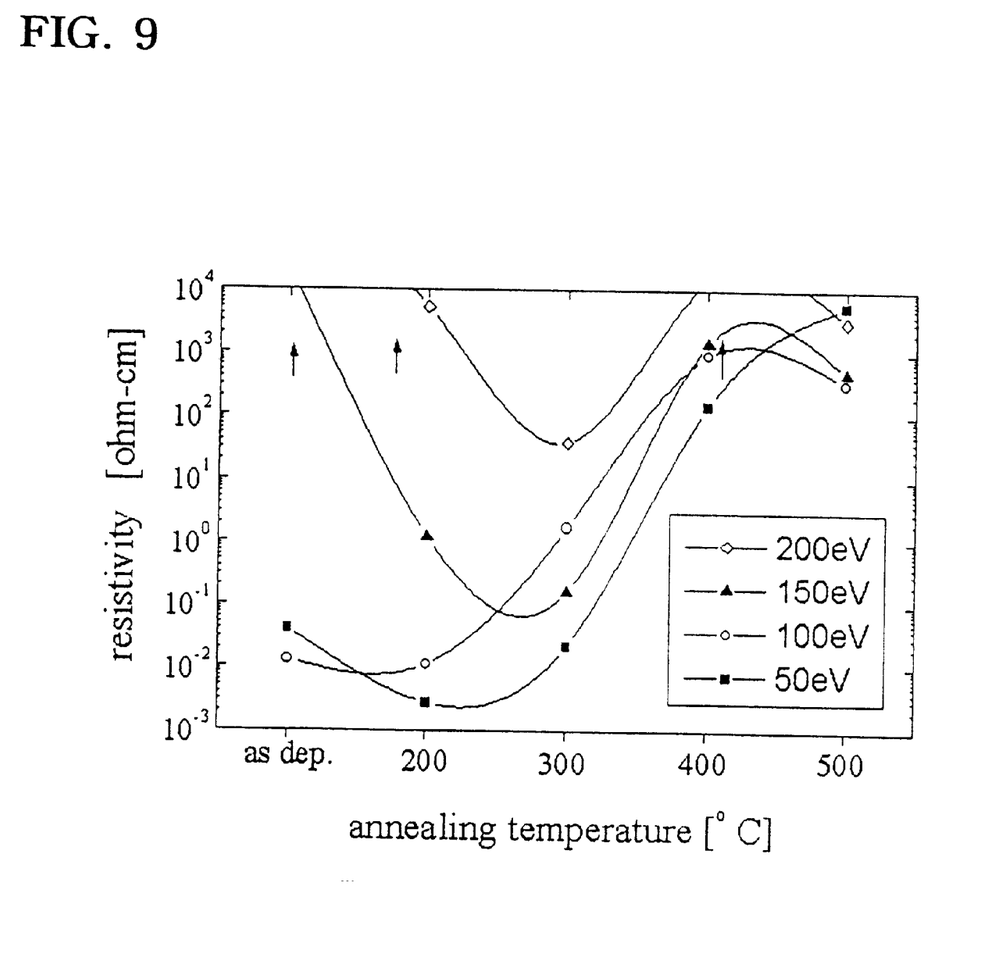
FIG. 9 is a plot of electrical resistivity of $SnO_2$ thin films produced by the process in the present invention as a function of annealing temperature.

The electrical resistivity of the $SnO_2$ films on glass substrate was measured by 4-point probe method. FIG. 9 is a plot of electrical resistivity of the $SnO_2$ films deposited from Sn target as a function of annealing temperature. As can be seen in the figure, all films after annealing them at 400° C. had resistivity higher than $10^2 \Omega$ cm. The films deposited from $SnO_2$ target, not shown in the figure, had even higher resistivity values beyond a measurable range. The high resistivity, along with the $SnO_2$ single phase formation, is a major factor in providing sensors with high sensitivity.

EXAMPLE 7

Fabrication of Gas Sensors

Figure 10:
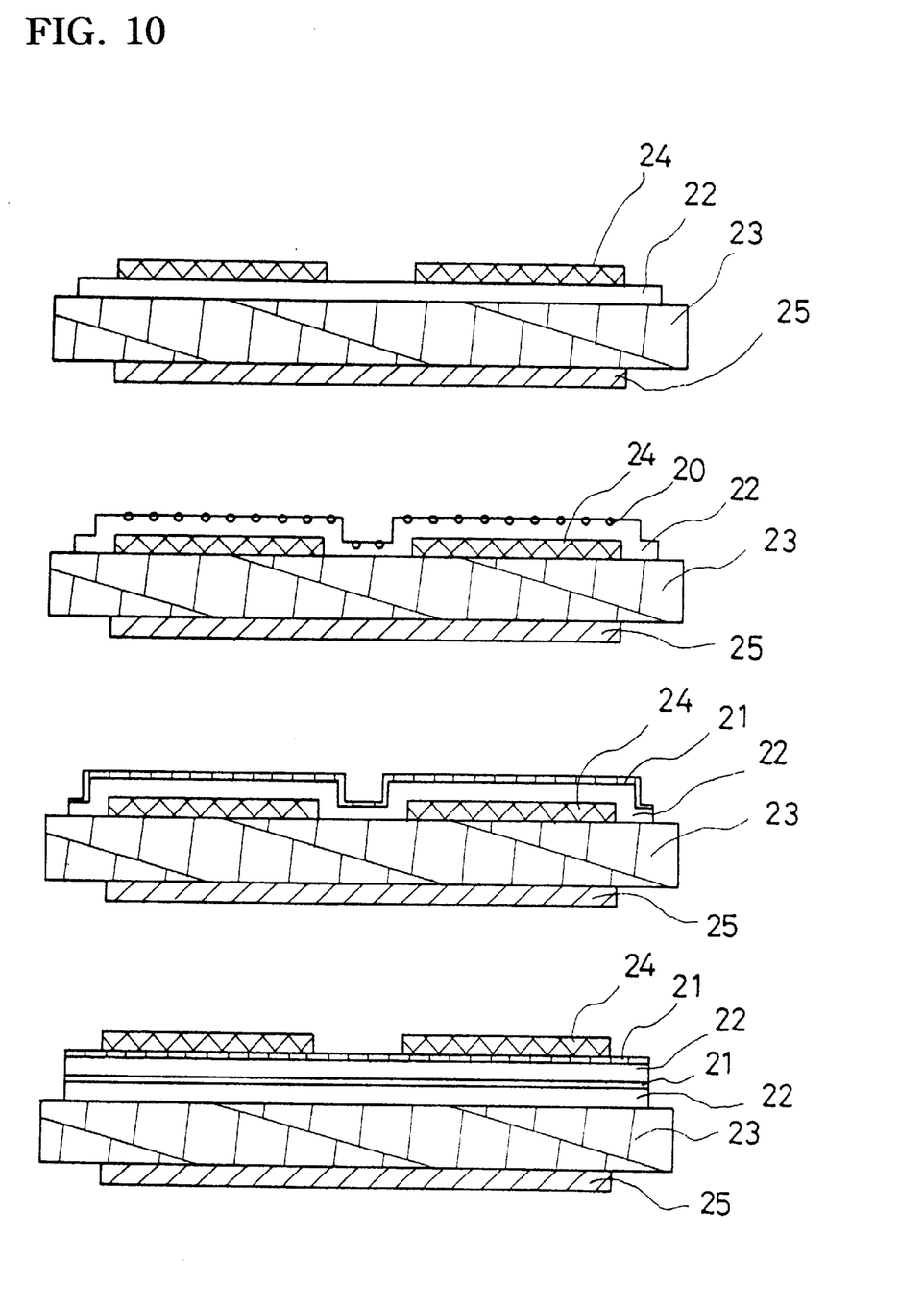
FIG. 10 are examples of thin film sensor configuration using $SnO_2$ detecting layers and CuO catalytic layers produced by the process in the present invention.

Shown in FIG. 10 are examples of sensor device application with $SnO_2$ sensing layers 22 and/or CuO catalytic layers 21 produced by the process in the present invention. A thin film heater 25 was placed on the backside of insulating substrate 23 such as $Al_2O_3$ or thermally oxidized Si. A pair of noble metal electrodes 24, such as Pt or Au, was located either on top or beneath the sensing layer. The $SnO_2$ sensing layer 22 may be used with or without surface catalyst 20 to provide sensitivity and selectivity. The CuO catalytic layer 21 is deposited on a n-type sensing layer such as $SnO_2$ to provide p-n junction, and the stack may be repeated.

Figure 11:
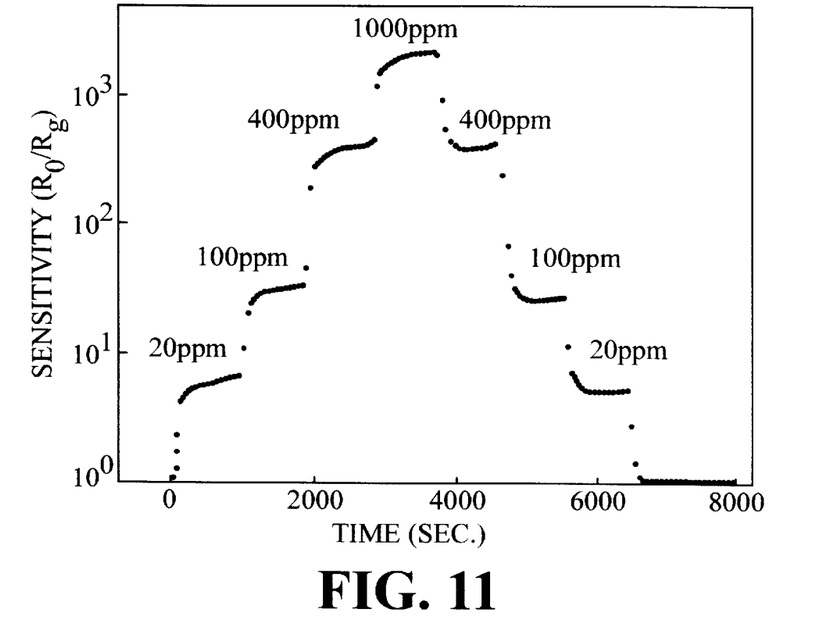
FIG. 11 is a plot of the hydrogen sensitivity of $SnO_2$ gas sensor doped with Pt as a function of time at various concentration.

FIG. 11 is a plot of a sensitivity response as a function of time against $H_2$ at 160° C. of $SnO_2$ thin film gas sensor added with Pt surface catalyst. Sensitivity is defined by the ratio between sensor's gas-induced resistance ($R_g$) and initial resistance ($R_o$). As can be seen in figure, the sensor showed good sensitivity higher than 1000 against $H_2$ of 400 ppm, linear change of sensitivity with gas concentration, and fast response time less than 1 minute.

Figure 12:
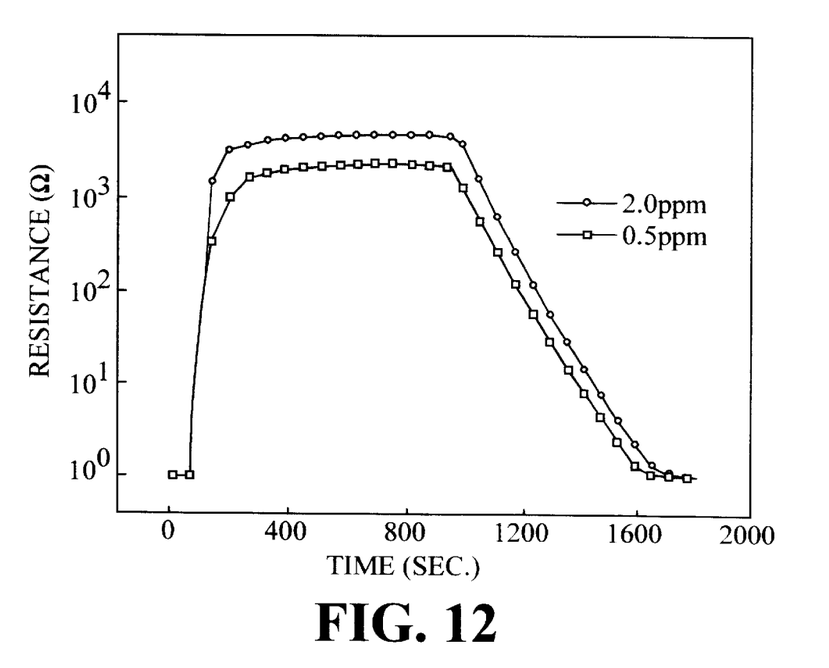
FIG. 12 is a plot of the hydrogen sulfide sensitivity of $SnO_2$/CuO double layer gas sensor as a function of time at various concentration.

FIG. 12 is a plot of a sensitivity response as a function of time against $H_2S$ at 160° C. of CuO-added $SnO_2$ thin film gas sensor. As can be seen in figure, the sensor showed good sensitivity higher than 1000 against $H_2S$ of 0.5 ppm and fast response time less than a few minutes. The foregoing detailed description of the process and example of the present invention has been given for clearness of understanding only and no unnecessary limitations should be understood therefrom. Some modifications will be obvious to those skilled in the art to which the invention permits, without deviation from the spirit of the invention as defined by the scope of the dependent claims.

What is claimed is:

1. A method for forming a CuO catalytic layer atop a gas sensing layer for a gas sensor device utilizing a dual ion beam sputtering apparatus, comprising the steps of:

sputter-depositing at least one of copper and copper-oxide atoms from a target onto a substrate using an argon ion gun; and simultaneously depositing oxygen atoms onto a gas sensing layer using an oxygen ion gun to produce a crystalline CuO layer having a thickness of approximately 0.1 nm to 10 nm to provide a p-n junction between the CuO layer and the gas sensing layer.

2. The method of claim 1, wherein the gas sensing layer is selected from Sn and Sn oxides.

3. The method of claim 1, wherein the acceleration energy of the argon ion beam is from 0.5 to 2.0 keV.

4. The method of claim 1, wherein the acceleration energy of the oxygen ion beam is from 0.0 to 500 eV.

* * * * *